United States Patent [19]  [11] 4,038,098
Wason [45] * July 26, 1977

[54] AMORPHOUS PRECIPITATED SILICEOUS PIGMENTS FOR COSMETIC OR DENTRIFICE USE AND METHODS FOR THEIR PRODUCTION

[75] Inventor: Satish K. Wason, Havre de Grace, Md.

[73] Assignee: J. M. Huber Corporation, Locust, N.J.

[*] Notice: The portion of the term of this patent subsequent to June 1, 1993, has been disclaimed.

[21] Appl. No.: 642,977

[22] Filed: Dec. 22, 1975

Related U.S. Application Data

[62] Division of Ser. No. 285,966, Sept. 5, 1972, Pat. No. 3,928,541.

[51] Int. Cl.$^2$ .............................................. C09C 1/30
[52] U.S. Cl. ................................. 106/288 B; 106/306; 106/309; 423/335; 423/339
[58] Field of Search ........................... 106/288 B, 306; 423/339, 335

[56] References Cited

U.S. PATENT DOCUMENTS 3,325,249  6/1967  Burke .................................. 423/339
3,424,602  1/1969  Nauroth ........................... 106/288 B
3,730,749  5/1973  Morgan ............................ 106/288 B

FOREIGN PATENT DOCUMENTS 710,015  11/1951  United Kingdom ................. 423/335

Primary Examiner—Winston A. Douglas
Assistant Examiner—J. V. Howard
Attorney, Agent, or Firm—Robert L. Price; Harold H. Flanders

[57] ABSTRACT

A method for producing precipitated silicic acid pigments and silicates having a unique combination of physical and chemical properties is disclosed. The pigments are produced by acidulating alkali metal silicate solutions which contain a salt or electrolyte, such as sodium sulfate, which serves to pre-polymerize the said silicate solution. Pigments produced in accordance with the invention exhibit lower wet cake moisture (or higher percent solids) and are characterized by their low structure, low oil absorption, high abrasiveness and high pack density. The products can be used as abrasive and polishing agents in dentifrice compositions, in the production of molecular sieves, in paints and the like. In a particularly advantageous embodiment, an adduct material, such as aluminum, is added to control the refractive index of the precipitated pigment.

9 Claims, No Drawings

AMORPHOUS PRECIPITATED SILICEOUS PIGMENTS FOR COSMETIC OR DENTRIFICE USE AND METHODS FOR THEIR PRODUCTION

This is a division of application Ser. No. 285,966, filed Sept. 5, 1972, now U.S. Pat. No. 3,928,541.

BACKGROUND OF THE INVENTION

The present invention relates to synthetic amorphous precipitated silicas, and more particularly, to a novel process for producing synthetic precipitated silicas and silicates having new and improved physical and chemical properties and which have particular use as an abrasive agent in toothpaste compositions.

As known in the art, finely divided amorphous precipitated silicic acid pigments and certain zeolitic type alumino silicates can be prepared by the acidulation of an aqueous silicate solution with an acid or a salt of the acid, such as aluminum sulfate. Such products are commercially available being sold, for example, under the trademarks "Zeo"; "Zeolex" and "Arogen" by the J. M. Huber Corporation. Specific examples of these products as well as methods for their preparation are disclosed in U.S. Pat. Nos. 2,739,073; 2,843,346 and 3,582,379.

In general, the nature or characteristics of the above discussed precipitated silicic acid (sometimes herein referred to as silicas) and silicate pigments depend, in part, on the chemistry of the silicate solution (specifically the $SiO_2/Na_2O$ ratio of the silicate) as well as the reaction conditions employed (precipitating pH, etc.). However such known pigments are characterized by, and have, the following properties: High structure, high wet cake moisture content, high oil absorption, low valley abrasion, high surface area and low pack density. In this regard, and due to the properties such as high oil absorption, high surface area, etc., the pigments have been widely and successfully used as reinforcing pigments in rubber, in paints, in the manufacture of paper, as moisture conditioners and the like.

However, the high wet cake moisture content is disadvantageous in that the drying and filtration rates are increased thus increasing the overall cost of the final product. For example, in the conventional production of silicic acid pigments as defined above, the wet cake moisture content of the product (following filtration of the precipitated reaction mass) is approximately 82%. This means that there can be recovered only 18 parts of dry pigment from 100 parts of wet cake.

Further, and very importantly, the low abrasiveness of known silica and silicate pigments renders then unsuitable for many uses. For example, it is well known that conventional synthetic precipitated silicates are unsuitable as polishing and abrasive agents in toothpaste compositions. See German Pat. No. 974,958; French Pat. No. 1,130,627; British Pat. No. 995,351; Swiss Pat. No. 280,671 and U.S. Pat. No. 3,250,680. In this regard, it is disclosed in U.S. Pat. No. 3,538,230 that known amorphous silicas such as precipitated silicas, pyrogenic silicas and aerogels are unsuitable for dentifrice use because of their initial small particle size and because of the ease in which they break down into small particle sizes which result in poor cleaning ability.

Further, conventional silicas and amorphous precipitated alumino silicates, such as "Zeolex" and "Arogen", cannot be used for a clear gel toothpaste because of their high refractive index (1.55) and because they lack the needed abrasive and polishing characteristics when added to the toothpaste base composition. Clear gel toothpaste contains a high percentage of abrasive and polishing agent in the toothpaste formula. The major function of the abrasive and polishing agent is to remove stains, food debris and bacterial plaque from the human tooth surface. Ideally the polishing agent should provide a maximum cleaning action at acceptable abrasion levels and must be compatible at high loadings of 15% up to 50% with other toothpaste formula ingredients. Thus the above noted silicas and alumino silicates are unsuitable for clear gel toothpastes, (such as the product sold under the trademark "Close-Up" by Lever Brothers), because they cannot be added at high loadings of 15% and above in a typical toothpaste composition. Also, because of their high oil absorption and high refractive index (1.55) known precipitated pigments thicken up the dentifrice composition and impart undesirable opacity to the base paste resulting in an unacceptable product.

More recently, however, and before turning to the details of the present invention, there has been developed, as disclosed in detail in U.S. Pat. No. 3,893,840, a process for producing siliceous pigments having improved physical and chemical properties including low structure, a low wet cake moisture content, high abrasion, low oil absorption and high pack densities. In accordance with the teaching of this application, the pigments are prepared by acidulating a solution of an alkali metal silicate with an acid until precipitation just begins. At this point the reaction mass is aged for a period of time and thereafter the acid addition is continued until the precipitated product is obtained. In accordance with one method embodiment disclosed by this application an adduct material, such as aluminum, is pre-mixed with the acid to control the refractive index of the pigment so that same may be employed in clear toothpaste composition.

The present invention is directed to a further method for producing silicic acid and silicate pigments having the aforementioned improved properties.

SUMMARY OF THE INVENTION

In summary, the present invention relates to the production of low structure, amorphous precipitated silicas and silicates from salt-induced polymerized alkali metal silicate solutions under controlled or predetermined reaction conditions. The new process for producing the low structure pigments does not require any reaction aging step. While the products of the invention are particularly suitable for use as a polishing and an abrasive agent in dentifrice compositions they can also be advantageously employed in further applications such as in the preparation of molecular sieves, as flattening and texturizing agents, as fillers and carriers, and as viscosity control agents.

In its broadest aspects, the method of the invention embodies the concept and is based on the discovery that low structure, high abrasion amorphous precipitated silicas and silicates can be prepared from alkali metal silicate (e.g., sodium silicate) solutions which have been pre-polymerized by the addition of an electrolyte, such as a sulfate salt of sodium, potassium or lithium. Stated differently, the novel process of the invention comprises the acidulation of salt-polymerized alkali metal silicate solutions to form silicic acid pigments having the aforementioned unique combination of physical and chemical properties. As will be discussed in more detail hereinbelow, the salt or the electrolyte is preferably an alkali metal salt of the acid used for acidulation. For example, if sulfuric acid is employed, the salt used to prepolymerize the silicate solution is preferably an alkali metal sulfate. Correspondingly, if the silicate is sodium silicate, then the salt would preferably be sodium sulfate.

In accordance with a further method embodiment it has been found that pigments of predetermined characteristics and properties can be produced if the acid and a portion of the alkali metal silicate are added simultaneously so that the reaction is carried out at either a predetermined or essentially constant pH. In accordance with a third and particularly advantageous method embodiment, the acidulating agent, such as sulfuric acid, is premixed with an adduct such as aluminum, which is preferably added as a water soluble salt thereof, as for example, aluminum sulfate to form an alumino silicate. In this regard it has been found that the addition of the adduct serves to control the refractive index of the resulting pigment while at the same time not substantially affecting the increase in the abrasiveness.

It is accordingly a general object of the present invention to provide a novel process for producing precipitated silicas having a unique combination of physical and chemical properties.

Another and more particular object is to provide improved synthetic amorphous precipitated silicas and silicate pigments which have particular utility for use as a cleaning and an abrasive agent in dentifrice compositions and a unique method for preparing said pigments.

Yet another object is to provide a highly efficient and improved process for producing silicic acid pigment which exhibits lower wet cake moisture or higher percent solids and which have high abrasion and low oil absorption characteristics.

Yet still another object is to provide novel synthetic amorphous precipitated siliceous pigments which are useful as abrasion and gelling agents in clear toothpaste compositions.

A further object is to provide a new process for producing precipitated amorphous silicas which have a unique balance of physical and chemical properties as compared to conventionally known precipitated pigments, said process further resulting in lower processing cost.

A still further object is to provide a process for producing low structure, low wet cake moisture, low surface area, low oil absorption, high valley abrasion and high pack density precipitated silicic acid and alumino silicate pigments.

Another object is to provide a new synthetic amorphous precipitated silica of controlled refractive index which is useful as a cleaning and polishing agent in a dentifrice composition and as a texturing agent in paint applications and other specialty areas.

The manner in which the foregoing and other objects are achieved in accordance with the present invention will be better understood in view of the following detailed description which discloses particularly advantageous method and composition embodiments for illustrative purposes.

DESCRIPTION OF PREFERRED EMBODIMENTS

As briefly discussed above, the present invention is based on the discovery that when salt-induced polymerized silicate solutions are acidulated, a wide range of low structure, low wet cake moisture, high abrasion precipitated pigments are obtained. In this regard, and again as briefly noted above, conventional precipitated silicas are prepared by the reaction of an aqueous silicate solution with an acid. The nature of the final silica produced depends, in part, on the nature of the silicate solution used for its preparation. For example it is generally accepted that commercially available sodium silicate solutions are more or less polymerized depending on their silica to sodium oxide ($SiO_2/Na_2O$) ratios. For example, sodium meta silicate (mole ratio unity) is known to be predominantly monomeric in character while water glass (mole ratio 3.3) is both monomeric and polymeric in character. In this regard it is also generally known that the nature of silicate solutions can be influenced by the presence of electrolytes such as sodium sulfate. Other salts such as alkali and alkaline earth salts can also influence the polymerization of sodium silicate solutions. Brady, Brown, and Huff (J. Colloid Sci 8, 256 (1953) found that addition of neutral salts such as sodium, potassium or lithium chloride or sulfate induces the polymerization of potassium silicate solution. Studies have shown that the rate of polymerization is proportional to the fourth power of the concentration of added salt and inversely proportional to the square root of the silicate concentration (Iler "The Colloid Chemistry of Silica and Silicates", page 28).

Notwithstanding the above and the somewhat extensive research activity in this art, it was not known, prior to the present invention, that salt-induced polymerized silicate solutions could be acidulated to form a precipitated pigment having the unique properties disclosed herein, i.e., high abrasion, low oil absorption, low wet cake moisture and high pack densities.

Turning now to more specific details, in the practice of the invention the salt or electrolyte, i.e., an alkali or alkaline earth salt is first added to a solution of the alkali metal silicate, e.g., sodium silicate, with the latter being pre-polymerized by the addition of the salt. In a preferred embodiment, the polymerization is such that the $SiO_2/Na_2O$ ratio is at least 2.0 and preferably in the range of from 2.3 to 2.7. The salt silicate solution is then heated to a temperature in the range of from 100° F to 200° F, preferably on the order of from about 150°–175° F. In general and except as otherwise expressly noted herein, the reaction temperatures and rates as well as the concentration of the reactants, i.e., the silicate solution and acid, are the same as in the above discussed known processes for producing precipitated silicic acid pigments. However, in the practice of the invention it has been found that particularly advantageous results are obtained if the concentration of the silicate solution is on the order of from about 1.0 to about 2.5 pounds/gallon. The acidulating agent or acid, e.g., sulfuric acid, is next charged to the reactor until the precipitation of the silicate is complete. In general the reaction should be carried out at a pH in the range of from about 6.5 to 11.0, it being of course understood that as the acid is added to the silicate solution, the pH will decrease as more acid is added. At the end of the precipitation, an excess of the acid is preferably added to bring the pH of the pigment within the range of from about 5.5 to 6.5 and the reaction mass is filtered, washed and dried.

In the first method embodiment, the entire solution of the salt induced polymerized silicate is initially charged to reactor. In a further embodiment, it has been found that a more homogeneous product and/or a product having predetermined properties can be obtained when from about one-half to two-thirds of the total silicate is initially charged to the reactor, and the remaining silicate is added simultaneously with the acid in a manner such that the reaction is carried out at a preset or a substantially constant pH, preferably in the range of from about 6.5 to 11.0. After the pigment has been precipitated, the pH of the resulting slurry may be reduced to from about 5.5 to 6.5 by the addition of an excess of the acid.

In a further method embodiment, it has been found that the refractive index of the precipitated pigment can be controlled by the addition of an adduct element (such as aluminum, magnesium and the like) to provide an abrasive or polishing agent for a clear translucent or transparent toothpaste composition. Thus in this embodiment, the acid is premixed with a solution of the adduct material i.e., aluminum (preferably in the form of a water soluble salt such as aluminum sulfate, etc.) and the acid-metal salt mixture is then used for acidulating the aqueous pre-polymerized alkali metal silicate. In accordance with the embodiment, the silicate solution may be initially added in its entirety to the reactor or may be partially combined with the acid-salt solution to maintain the pH of the reaction medium at the desired level.

At this point it may be noted that as used herein the term "structure" is intended to include, and is defined as, the ability of a silica material to hold water in its wet cake. When silicas, such as the aforementioned conventional precipitated silicas, hold a high percentage of water, i.e., in the neighborhood of 75% to 85%, they are known and referred to as high structure silicas. Materials holding less than 75% and preferably in the neighborhood of from about 50% to 70% water in their wet cake are referred to as low structure silicas.

As will be seen from the above, the starting materials or reactants include an alkali or alkaline earth metal salt (the electrolyte); an alkali metal silicate; an acid, and a watersoluble salt of an alkaline earth metal or aluminum. In the present invention the silicate is preferably treated or pre-polymerized (as defined herein) by the addition of a sodium, potassium or lithium salt. The salt should preferably correspond to the acid employed; i.e., if sulfuric acid is employed for the acidulation, then the electrolyte would comprise sodium, potassium or lithium sulfate. The preferred salt and acid are sodium sulfate and sulfuric acid, respectively. However, other salts, including the alkaline earth metal salts, such as calcium or magnesium sulfate or nitrate, may be employed to pre-polymerize the silicate solution. As used herein the term alkali metal silicates include all the common forms of alkali silicates, as for example, metasilicates, disilicates and the like. Water soluble potassium silicates and sodium silicates are particularly advantageous. Because of their relatively low cost, sodium silicates are preferred. Although the commercially available silicate solutions may be more or less polymerized depending on their silica to sodium oxide ($SiO_2/Na_2O$) ratios, the addition of the electrolyte to the silicate solution is critical. While not completely understood, it is thought that the presence of the salt in the silicate solution influences the size of the silica micelles such that a large number of small micelles are first formed which attach themselves to form particles and aggregates. In this sense, the salt may serve as a nucleating agent and the term "polymerized" as set forth herein is intended to include such theory.

While the acidulating agent or acid is preferably a strong mineral acid, such as sulfuric acid, nitric acid and hydrochloric acid, it should be understood that other acids, including organic acids, as for example, acetic acid, formic, or carbonic acid can be employed. The adduct material, employed to control the refractive index of the precipitated product is preferably an alkaline earth metal such as magnesium, calcium or aluminum. As previously noted, the adduct is preferably employed in the form of a watersoluble salt of the metal. For example, aluminum salts useful in the method of the invention are the water soluble salts of aluminum and strong acids such as aluminum sulfate, aluminum chloride, aluminum nitrate, and ammonium alum. The acidulating agent or acid is preferably added as a dilute solution thereof. Preferred results are obtained if the acidic solution is from about 10 to 25% by weight acid based on the total weight of the solution. However this may vary depending upon the particular acid employed, etc., as is known in the art.

As should be readily appreciated by those skilled in the art, no special equipment is required in the methods herein described. In this regard, however, the reactor should be equipped with heating means, e.g., a steam jacket, in order to maintain the desired reaction temperature and should have adequate agitating means to produce a strong backflow on the body of the liquid and thus avoid zones of high concentration of the incoming reactants. It is desirable to bring the reactants together so as to produce an instantaneous reaction of all material being fed to the fullest extent reasonably possible, as such promotes uniformity of the resulting products. Storage vessels (for the reactants) connected to the reaction vessel through lines fitted with flow control means may also be provided. The reaction vessel may be equipped with an outlet line leading to a filter which may be of conventional design. As noted above, the filtered mass is washed and dried. Such steps may also be conducted in conventional equipment, it being understood, of course, that same do not form a part of the present invention.

If the pigments of the invention are used in toothpaste compositions, the dentifrice (if in the form of a paste) may contain humectant materials and binders to give the dentifrice a smooth texture and good flowability. Gylcerine, sorbitol, corn syrup, glucose and the like may be used as carriers. Examples of binders include gum tragacanth, sodium carboxymethylcellulose and the like. The above materials as well as specific formulations and ingredients of toothpaste compositions are well known in the art and are disclosed in numerous publications and e.g., in U.S. Pat. Nos. 2,994,642 and 3,538,230.

The invention will be further illustrated by the following examples which set forth particularly advantageous method and composition embodiments. While the examples serve to illustrate the present invention, they are not intended to limit it thereto.

EXAMPLE 1

In this experiment, 5% sodium sulfate was added to a sodium silicate solution (containing 1.24 lbs/gallon silicate having an $SiO_2/Na_2O$ mole ratio of 2.5). Ten (10) gallons of the silicate solution containing the 5% sodium sulfate was charged to a stirrer reactor. The silicate solution, containing the salt, was heated to 175° F. Sulfuric acid of 11.4% concentration was then added to the reactor at the rate of 0.12 gallons per minute until a pH of 5.8 was reached. The silica slurry was stabilized for 20 minutes at 200° F, and the final pH was adjusted to between 5.8-6.0. The resulting silica slurry was filtered, washed, dried and milled in the conventional manner. It was found that the presence of the salt in the initial silicate solution influences the size of silica micelles such that a large number of small micelles are first formed which attach themselves to form particles and aggregates. The particles, resulting from the reaction of salt containing silicate and acid, result in a low structure silica of lower wet cake moisture than the conventional precipitated silica produced from salt free silicate solution. Further tests established that a range of low structure silicas could be prepared by maintaining the precipitation pH substantially constant and within the range of pH 7-10.

EXAMPLE 2

The procedure of Example 1 was repeated except that 10% sodium sulfate was added to the silicate prior to making the low structure silica batch.

EXAMPLE 3

In this example, 70 gallons of 1.24 lbs/gallon sodium silicate solution containing 10% sodium sulfate were added to the stirred reactor and the solution was heated to 175° F. Sulfuric acid of 11.4% concentration was added to the reactor at the rate of 0.84 gallons per minute until a pH of 5.8-6.0 was obtained. The reaction slurry containing silica particles was stabilized by heating to 200° F for 20 minutes. The final pH was readjusted between 5.8-6.0. The batch was then processed in the conventional manner.

EXAMPLE 4

In this experiment, 35 gallons of 1.24 lbs/gallon silicate solution containing 10% sodium sulfate were added to the stirred reactor and the solution was heated to 175° F. Sulfuric acid of 10.6% concentration was added to the reactor at preset rates until a reaction pH of 10.1 ($\pm 0.1$) was obtained. At this stage, both the acid and a silicate solution (1.24 lbs/gallon concentration and containing 10% sodium sulfate) were added to the reactor at the rate of 0.84 and 1.4 gallons per minute respectively. The silicate addition was continued for only 25 minutes and then it was stopped. The acid addition was continued until a final pH of 5.5 was obtained. The batch was then processed similar to Example 1.

EXAMPLE 5

The procedure of Example 3 was repeated except that no sodium sulfate was added to the silicate prior to making the silica pigment. This batch was prepared as a control batch to compare the properties of conventional silica with the low structure silicas produced in accordance with the teachings of the present invention.

The properties of the low structure silicas of Examples 1-4 are summarized in the following table.

TABLE 1

| Example | % Sodium Sulfate in Silicate | % Wet Cake Moisture | S A($m^2$/g) | Oil Absorption cc/100g | Density lbs/cu ft Pour | Density lbs/cu ft Pack | Valley Abrasion mg wire loss |
|---|---|---|---|---|---|---|---|
| 1 | 5 | 70 | 62 | 136 | 10.2 | 20.5 | 11.6 |
| 2 | 10 | 66 | 72 | 118 | 13.3 | 25.0 | 21.6 |
| 3 | 10 | 70 | 45 | 140 | 9.4 | 17.6 | 13.4 |
| 4 | 10 | 64 | 52 | 91 | 13.3 | 25.0 | 26.0 |
| 5 | Control-0 | 82 | 150 | 211 | 6.3 | 10.7 | 2.5 |

From the above it is clearly established that the new process results in silicas of lower structure, lower wet cake moisture, lower oil absorption, lower surface area, higher pack density and higher valley abrasion than the conventional precipitated silica (note Example 5).

As discussed above, conventional precipitated silicas cannot be used at high loadings in a toothpaste base composition because of the thickening effect and also because they are cosmetically unacceptable and result in poor cleaning properties. On the other hand, the low structure silicas of Examples 1 thru 4 can be used at high loading without affecting the viscosity of the dentifrice composition.

The MSA particle size distribution of the unique low structure silicas of the invention are listed in Table II. The average particle size and the size distribution of the low structure silicas can be controlled by controlling the processing parameters.

TABLE II

MSA Particle Size Distribution of Silicas of Examples 1-5
MSA % By Weight Less Than Size, Particle Size Microns

| Example | 30 | 20 | 15 | 10 | 5 | 3 | 1 | 0.5 | 0.3 | Average Size |
|---|---|---|---|---|---|---|---|---|---|---|
| 1 | 93 | 80 | 72 | 51 | 33 | 22 | 8 | 1 | 0 | 9.5 |
| 2 | 96 | 89 | 79 | 61 | 38 | 24 | 7 | 2 | 0 | 7.4 |
| 3 | 99 | 98 | 93 | 82 | 51 | 39 | 12 | 2 | 0 | 4.6 |
| 4 | 98 | 94 | 87 | 71 | 43 | 33 | 11 | 4 | 0 | 6.0 |
| 5 | 96 | 93 | 82 | 60 | 32 | 21 | 6 | 0 | 0 | 8.0 |

EXAMPLE 6

In a series of tests the general procedures of Examples 1-5 were repeated except that the precipitating pH was varied by controlling the rate of the addition of the acid. The results of these tests clearly established that the properties of the pigments (i.e., particle size, etc.) could be controlled within predetermined limits by controlling the processing parameters.

EXAMPLE 7

The general procedure of Examples 1-6 was repeated except that nitric acid, hydrochloric acid, acetic acid and formic acid were substituted for the sulfuric acid. The results were substantially the same as in Examples 1-6. The corresponding salts (to polymerize the silicate) were also employed as e.g., sodium nitrate.

EXAMPLE 8

In a series of tests the general procedures of Examples 1-7 were repeated except that aqueous sodium silicates having mol ratios ($SiO_2/Na_2O$) in the range of from 1 to 3 were substituted for the 2.5 silicate of Examples 1-7. The results were substantially the same as in Examples 1-7 except that it was found that the use of alkali metal silicates having an $SiO_2/Na_2O$ mol ratio within the range of from about 2.0 to 2.7 resulted in reduced and optimum wet cake moisture contents.

EXAMPLE 9

The general procedures of Examples 1–8 were repeated except that potassium sulfate and lithium sulfate were substituted for the sodium sulfate. The corresponding silicate, i.e., potassium and lithium sulfate, was also employed. The results of this Example was substantially the same as in Examples 1–8.

EXAMPLE 10

The procedures of Examples 1–9 were repeated except that the amount of the sulfate employed was varied from 5 to 20% (by increments of 3%). The results were substantially the same as in Examples 1–9.

The following Examples serve to illustrate the method embodiment of the invention wherein low structure alumino silicates are prepared from salt-induced polymerized silicate solutions.

EXAMPLE 11

In this example 10% sodium sulfate was added to 70 gallons of 1.24 pounds per gallon silicate of silica-to-sodium oxide molar ratio of 2.6 to pre-polymerize silicate by the presence of salt. This silicate solution was introduced to a stirred reactor and heated to 175° F. Aluminum sulfate of 1.38 lbs/gallon concentration was pre-mixed with 11.4% sulfuric acid in the volume ratio 11.4 to 100. This mixed aluminum sulfate-acid solution was used for the precipitation of alumino silicate of controlled refractive index. The acid-aluminum sulfate solution was added to the reactor until a final pH of 6.0 was obtained. The reaction slurry was digested for 20 minutes at 200° F and the final reaction pH readjusted to 5.5 The reaction slurry was filtered, washed, dried and milled in the conventional manner.

A novel aspect of the new process is the production of precipitated alumino silicate from salt-induced pre-polymerized sodium silicate solutions. The presence of salt in the silicate influences the size of micelles such that a large number of small alumino silicate micelles are first formed which combine to form particles and aggregates. The alumino silicates produced via the new process, results in lower wet cake moisture, lower structure, lower oil absorption and higher abrasion than the conventional precipitated alumino silicate produced from salt-free silicate solutions.

In a series of further tests it was found that a range of low structure alumino silicates of controlled refractive index and abrasive and polishing characteristics for use in clear gel toothpaste could be prepared by maintaining the precipitation pH substantially constant and within the range of pH 7–10.

EXAMPLE 12

The procedure of Example 11 was repeated by adding 35 gallons of the silicate-salt solution to the reactor and neutralizing with the mixed acid-aluminum sulfate solution until pH 10.1 plus or minus 0.1 was obtained. At this stage, the remaining 35 gallons of the silicate was added with the simultaneous acid-aluminum sulfate addition. Silicate was turned off in 25 minutes and the acid-aluminum sulfate addition was continued until a final slurry pH of 5.5 was reached. The batch was then processed similar to Example 11 above.

EXAMPLE 13

A control experiment was performed in which Example 11 was repeated except that the silicate solution was free of sodium sulfate.

The results of Examples 11–13 are summarized in the following Table.

TABLE III

| Ex. | Description | % Wet Cake Moisture | Surface Area ($m^2/g$) | Oil Absorption (cc/100g) | Valley Abrasion |
|---|---|---|---|---|---|
| 11 | SAS* from Sulfate System | 70 | 367 | 138 | 20 |
| 12 | SAS from Sulfate System | 64 | 395 | 91 | 26 |
| 13 | Control —No Sulfate | 82 | 366 | 202 | 7 |

*SAS = Sodium alumino silicate

From the above data, it is clear that the unique process of the invention results in alumino silicates of lower wet cake moisture, lower structure, lower oil absorption and higher valley abrasion than the conventional precipitated alumino silicate. Tests established that the alumino silicate of Example 13 (control) cannot be used in the clear gel toothpaste because it thickens up the toothpaste base composition, and it does not provide the needed polishing and abrasive characteristics to the paste for cleaning human teeth. Because of its high oil absorption and vehicle demand, the control (Example 13) alumino silicate cannot be used at high loadings without affecting the viscosity of the dentifrice composition.

EXAMPLE 14

In a series of tests the general procedures of Examples 11–13 were repeated except that nitric acid, hydrochloric acid, acetic acid and formic acid were substituted for the sulfuric acid. The results were substantially the same as in Examples 11–13.

EXAMPLE 15

In a series of further tests the procedures of Examples 11–13 were repeated except that the precipitating pH as well as the $SiO_2/Na_2O$ mol ratio of the silicate were varied in the manner as shown above in Examples 6 and 8. The results were substantially the same except with regard to those variables and results noted in Examples 6 and 8.

EXAMPLE 16

The general procedures of Examples 11–15 were repeated except that potassium sulfate and lithium sulfate was substituted for the sodium sulfate. The results were substantially the same.

EXAMPLE 17

In a series of tests the general procedures of Examples 1–16 were repeated except that the reaction temperature was varied within the range of from 125° to 200° F. The results were substantially the same as in the above examples. Other process variables including the rate of the addition of the acid, etc. were also varied within the limits set forth in the instant specification and those of the above discussed conventionally known processes. It was found that such process variables were important from the standpoint of optimum reaction rates, etc. and from the standpoint of using predetermined reaction conditions (pH, etc.) to obtain a product of predetermined characteristics, i.e., a particular moisture content, etc.

EXAMPLE 18

The general procedure of the above Examples were generally repeated except that alkaline earth metal salts including calcium and magnesium sulfate were substituted for the sodium, potassium or lithium salts used to pre-polymerize the silicate solution. Other salts, e.g., magnesium nitrate (here employing nitric acid as the acidulating agent) were also employed. The results were substantially the same. In still further tests, calcium and magnesium sulfates were employed as the adduct material to control the refractive index. These tests were successful but established that optimum results were obtained when employing aluminum as the adduct.

From the above it will be seen that the process of the instant invention results in new products having a unique combination of physical and chemical properties. These include, e.g., low oil absorption, i.e., on the order of less than 125 cc/100 g, wet cake moisture contents of less than 70%, surface areas of less than 100 $m^2/g$ when the adduct material is not added and in the range of from about 100-300 when the latter is employed; pack densities of greater than 12 lbs/ft$^3$ and valley abrasions of greater than 5 (mg. wire loss). Improved and very important processing advantages are also obtained. These include lower processing costs and better packaging characteristics. While particular embodiments have been disclosed for illustrative purposes, the invention is not intended to be limited thereto. For example, in the case of pigment production for a special utility the precipitating pH and the final slurry pH may be tailored accordingly. Other improved properties of the invention include controlled particle size, better dispersion and improved wetting and viscosity characteristics. As indicated above, such properties are obtained and controlled by changing or pre-selecting the precipitation pH and other processing parameters such as the order of the addition of the silicate solution, as per for example, the second method embodiment. In further tests, it was established that the unique pigment of the invention had properties similar to those disclosed in the aforementioned U.S. Pat. 3,893,840 and could also be advantageously employed in the production of molecular sieves (faujasite); in flatting applications and the like as disclosed in Example 29 and Tables 4 and 5 of the said application.

As used herein, the term "pigments" is not intended to be limited to color-bearing materials which impart color to other substances or mixtures, but is intended to refer to the finely divided, powdery nature of the materials, such as silica, silicon dioxide, precipitated silica, silica abrasives, sodium alumino silicates, and the like, which are also in other contexts referred to as fillers, extenders, and reinforcing pigments.

What is claimed is:

1. A method for producing an amorphous precipitated silicic acid having improved chemical and physical properties including high abrasiveness and low wet cake moisture content prior to the drying thereof, said process comprising the steps of:
    1. contacting an aqueous solution of an alkali metal silicate with an alkali or alkaline earth metal salt to prepolymerize said alkali metal silicate and form an aqueous solution of prepolymerized alkali metal silicate solution;
    2. combining an acid with an adduct material selected from the group consisting of the water soluble salts of aluminum and alkaline earth metals to form an acidulating solution;
    3. acidulating said prepolymerized aqueous alkali metal silicate solution with said acidulating solution by addition of the solution to said prepolymerized silicate solution;
    4. continuing the addition of said acidulation solution to said aqueous silicate solution until the precipitation of said silicic acid is complete; and
    5. separating and recovering the precipitated silicic acid;

wherein said adduct material combined with said mineral acid is effective to control the refractive index of the precipitated silicic acid and form an alumino or alkaline earth metal silicate.

2. The method in accordance with claim 1, said method further comprising the steps of drying and disintegrating the precipitated material.

3. The method in accordance with claim 1 wherein said acid is a mineral acid selected from the group consisting of sulfuric acid, nitric acid and hydrochloric acid and said salt used to prepolymerize said silicate solution is a salt of the said sulfuric acid, nitric acid or hydrochloric acid, respectively.

4. The method in accordance with claim 3 wherein said alkali metal silicate is selected from the group consisting of sodium silicate, potassium silicate and lithium silicate.

5. The method in accordance with claim 4 wherein said alkali metal silicate has a $SiO_2/X_2O$ mol ratio in the range of from about 1.0 to 3.0 wherein X is selected from the group consisting of sodium, potassium and lithium.

6. The method in accordance with claim 1 wherein said adduct material is selected from the group consisting of the water soluble salts of aluminum, magnesium and calcium.

7. The method in accordance with claim 6 wherein said adduct material is aluminum sulfate and said mineral acid is sulfuric acid.

8. The product produced by the process of claim 1.

9. The product produced by the process of claim 7.

* * * * *